United States Patent [19]

Taylor, Jr. et al.

[11] Patent Number: 5,095,014

[45] Date of Patent: Mar. 10, 1992

[54] 3-(2-CHLORO-4-(TRIFLUOROMETHYL)-PHENOXY)-1-AZETIDINE CARBOXAMIDES HAVING ANTICONVULSANT ACTIVITY

[75] Inventors: Chandler R. Taylor, Jr.; Albert D. Cale, Jr., both of Mechanicsville; Harold F. Stauffer, Jr., Midlothian, all of Va.

[73] Assignee: A. H. Robins Company, Incorporated, Richmond, Va.

[21] Appl. No.: 623,517

[22] Filed: Dec. 7, 1990

[51] Int. Cl.$^5$ .................. A61K 31/395; C07D 205/04
[52] U.S. Cl. ..................... 514/210; 548/952
[58] Field of Search .......... 514/210; 548/952

[56] References Cited

U.S. PATENT DOCUMENTS

| | | | |
|---|---|---|---|
| 4,226,861 | 10/1980 | Cale | 548/952 X |
| 4,571,393 | 2/1986 | Teng | 514/210 |
| 4,956,359 | 9/1990 | Taylor et al. | 514/210 |

Primary Examiner—Mary C. Lee
Assistant Examiner—Jacqueline Haley
Attorney, Agent, or Firm—Donald E. Gillespie

[57] ABSTRACT

The present invention relates to novel 3-(2-chlor-4-trifluoromethylphenoxy)-1-azetidine carboxamides having the formula:

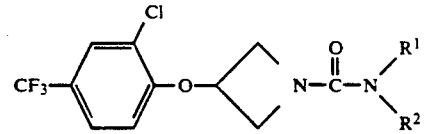

wherein R1 and R2, same or different, are selected from hydrogen, $C_1$–$C_4$ alkyl, and allyl.

In a series of 3-(substitutedphenoxy)-1-azetidinecarboxamides, introduction of a chlorine atom at the 2-position of the phenoxy group of the corresponding 4-trifluoromethylphenoxy-1-azetidinecarboxamides resulted in unexpected increased potency in anticonvulsant pharmacological tests.

6 Claims, No Drawings

3-(2-CHLORO-4-(TRIFLUOROMETHYL)PHENOXY)-1-AZETIDINE CARBOXAMIDES HAVING ANTICONVULSANT ACTIVITY

BACKGROUND OF THE INVENTION

1. Field of Invention

The present invention relates to novel 3-(2-chloro-4-trifluoromethylphenoxy)-1-azetidine carboxamides which exhibit anticonvulsant activity, compositions thereof and methods of making and using same.

2. Information Disclosure Statement

U.S. Pat. No. 4,226,861 discloses anticonvulsant activity of novel compounds useful for treating epilepsy having the formula:

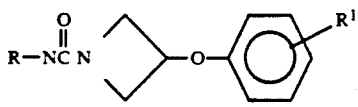

where R is loweralkyl and $R^1$ is hydrogen, aminocarbonyl, or trifluoromethyl. Our U.S. Pat. No. 4,571,393 discloses compounds having prolonged anticonvulsant activity of the formula:

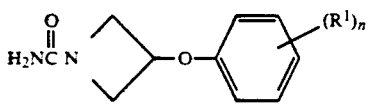

wherein $R^1$ is selected from hydrogen, fluoro, loweralkyl, loweralkoxy, trifluoromethyl, acetyl, or aminocarbonyl; and n is 1-3 and when n is 2 or 3, the $R^1$ selections may be the same or different. U.S. patent applications Ser. Nos. 921,466 and 921,521, filed Oct. 22, 1986, broadly disclose compounds of the formula:

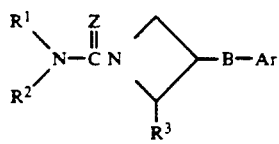

having anticonvulsant, muscle relaxant, and antianxiety activities. In the above formula B and Z are O or S independently, Ar includes phenyl substituted by one or two radicals selected from chloro, bromo, fluoro, loweralkyl, loweralkoxy, nitro, amino, carbonyl, or trifluoromethyl; and $R^1$, $R^2$, and $R^3$ can be selected independently from a group consisting in part of hydrogen, loweralkyl, aryl, and alkyl.

SUMMARY OF THE INVENTION

The novel compounds of this invention are represented by the formula:

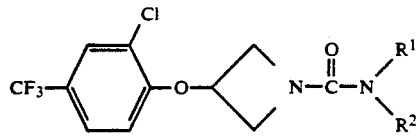

where $R^1$ and $R^2$, same or different, are selected fro hydrogen, $C_1$–$C_4$alkyl, and allyl. Whereas the compounds of this invention are broadly described in the aforementioned U.S. Patent Applications and in U.S. Pat. No. 4,571,393 which encompass 3-(phenoxy)-1-azetidinecarboxamides where the phenyl group can have more than one substituent, the 3-[2-chloro-4-(trifluoromethyl)phenoxy]-1-azetidinecarboxamides disclosed herein represent a unique group of disubstituted compounds that displayed unexpected potency over other 3-(di-substituted phenoxy)-1-azetidinecarboxamides.

The pharmacological tests used are (1) maximal electroshock and (2) pentylenetetrazole (Metrazole®) chemical challenge where the percent protection afforded by the test compounds against convulsions induced by electrical stimulus or by the drug Metrazole is determined. These test procedures are described further hereinbelow.

Generally, anticonvulsant drugs which exhibit greater protection against the Metrazol challenge are considered to be useful in treating the absence type epileptic seizure and those that exhibit greater potency against the electrically induced convulsions are useful against the partial-type of epileptic seizure. Selective protection against the Metrazole or electrically-induced convulsions is demonstrated by compounds of this invention.

Therefore it is an object of this invention to provide novel anticonvulsant compounds which can be useful in treating both the absence and partial type of epileptic seizures.

It is another object of this invention to provide novel anticonvulsant compounds which can be useful in treating absence type seizures.

DETAILED DESCRIPTION OF THE INVENTION

The compounds of this invention are prepared from 1-diphenylmethyl-3-azetidinol according to the following reaction sequence:

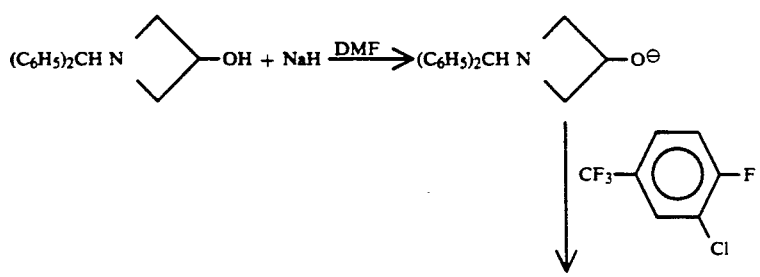

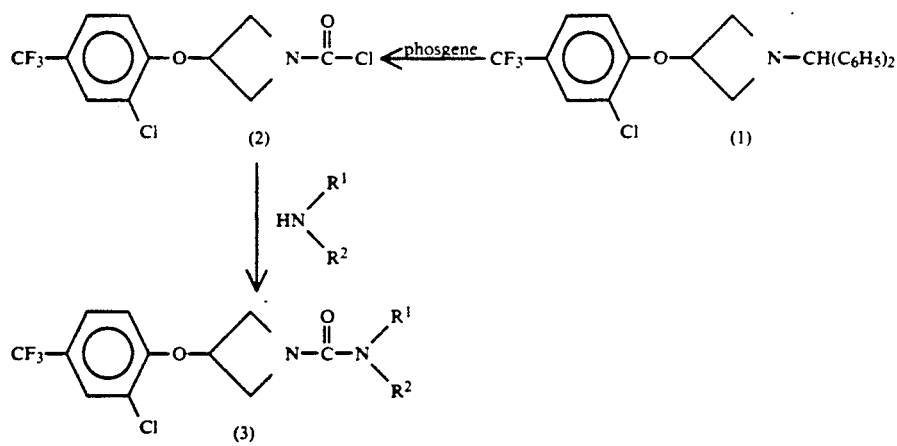

Alternatively the intermediate (1) could be hydrogenated by known procedures to remove the diphenylmethyl group and the resulting 3-[2-chloro-4-(trifluoromethyl)phenoxy]azetidine reacted with an appropriate alkyl isocyanate, dialkylcarbamyl chloride or nitrourea to obtain the invention compound (3).

The following Preparations and Examples illustrate the above reaction scheme and can be carried out without undue experimentation by one skilled in the art. These Preparations and Examples are illustrative of the invention and not to be construed as limiting to this disclosure in any way. The various reagents used are either commercially available or readily synthesized by procedures given in the chemical and patent literature. The aforementioned U.S. patents and applications disclose synthetic procedures for intermediates incorporated herein.

PREPARATION 1

3-[2-Chloro-4-(trifluoromethyl)phenoxy]-1-(diphenylmethyl)azetidine monohydrochloride A stirred slurry of 3.1 g (0.077 mol) of sodium hydride (60% in mineral oil) in 50 ml of dry dimethylformamide under nitrogen was heated to 80° C. and 17 g (0.07 mol) of 1-(diphenylmethyl)-3-azetidinol in 70 ml of dry dimethylformamide was added dropwise at a rate which gave a steady evolution of hydrogen and the temperature was maintained below 90° C. The reaction mixture was then heated for 1 hour at 90°-100° C. followed by the addition of 13.9 g (0.07 mol) of 3-chloro-4-fluorobenzotrifluoride. The reaction mixture became exothermic (117° C.) and after cooling was maintained at 100°-110° C. for 16 hr. The reaction mixture was treated with 1.5 g (0.04 mol) of sodium hydride and heated for an additional 18 hr. The reaction mixture was cautiously poured into ice water and the oil which separated was extracted into benzene (3×100 ml). The extracts were combined and concentrated in vacuo (39.32 g). The residue was chromatographed on a 400-g silica gel column by eluting with a methanol: methylene chloride gradient followed by washing with 50:50 methanol: methylene chloride to yield 21.1 g of crude product. A sample was converted to the hydrochloride salt and recrystallized from ethyl acetate/ethyl ether at room temperature to yield 1 g of white powder-like crystals, mp 108°-114° C.

Analysis: Calculated for $C_{23}H_{19}ClF_3NO \cdot HCl$: C, 60.81; H, 4.44; N, 3.08. Found: C, 60.39; H, 4.45; N, 3.09.

PREPARATION 2

3-[2-(Chloro-4-(trifluoromethyl)phenoxy]-1-azetidinecarbonyl chloride

A stirred solution of 5.3 g (0.054 mol) of phosgene in 50 ml of methylene chloride was cooled in a tap water bath and treated with 18.6 g (0.045 mole) of 3-[2-chloro-4-(trifluoromethyl)phenoxy]-1-(diphenylmethyl)azetidine in 25 ml of methylene chloride, added dropwise. The reaction mixture was stirred for 16 h as it warmed to ambient temperature, then treated with ice water to destroy the excess phosgene. The methylene chloride layer was separated, dried over magnesium sulfate and concentrated in vacuo (23 g). The residue was triturated with hexane and decanted. The second trituration of the residue resulted in the formation of a crystalline product which was collected by filtration to obtain 8.9 g (63%). A sample was recrystallized from hexane with charcoal treatment, mp 86°-88°.

Analysis: Calculated for $C_{11}H_8Cl_2F_3NO_2$: C, 42.07; H, 2.57; N, 4.46. Found: C, 42.02; H, 2.51; N, 4.48.

PREPARATION 3

3-(2-Chlorophenoxy)-1-(diphenylmethyl)azetidine ethanedioate (2:3)

A mixture of 48 g (0.2 mole) of 1-(diphenylmethyl)azetidin-3-ol and 22 g (0.22 mol) of triethylamine in 800 ml of toluene was stirred under nitrogen while cooling to 5° C. in an ice bath. The reaction mixture was treated by the dropwise addition of 25.2 g (0.22 mol) of methanesulfonyl chloride, then stirred at ambient temperature for 2 h. The reaction mixture was treated with ice water to dissolve the triethylamine hydrochloride and transferred to a separatory funnel where the aqueous portion was removed and the organic portion washed with ice water (200 ml). The organic portion was returned to the reaction flask and treated with 28.3 g (0.22 mol) of 2-chlorophenol, 26.4 g (0.66 mol) of sodium hydroxide in 100 ml of water, and 50 mg (0.1% by weight) of tetrabutylammonium bromide, then heated to reflux. After stirring for 23 h at reflux, thin layer chromatographic analysis (tlc) (10% methanol/methylene chloride on silica gel) showed about 60% product and the decomposition of the mesylate back to the starting azetidinol. The reaction mixture was allowed to cool and transferred to a separatory funnel where the basic layer was removed and the toluene portion washed with water (2×200 ml), dried over magnesium sulfate, and then concentrated in vacuo to obtain 81 g. The residue was dissolved in 2-propanol and treated with 15 g of oxalic acid dissolved in hot 2-propanol. The solid which precipitated was triturated in boiling 2-propanol, cooled and filtered to yield 78.8 g of product as the oxalate salt. Tlc (20% methanol/benzene on silica gel) showed 3 compounds. The crude product was converted to the free base by standard methods, and the residue (60.8 g) was placed on a 600 g Florisil column and eluted with benzene followed by an acetone/benzene gradient (1–5% acetone). When the mesylate product was removed from the column, the gradient was increased to 10–20% acetone. The product was eluted from the column in 6 (250 ml) fractions which were combined and concentrated in vacuo to give 36.6 g (52.3%) of pale yellow oil. A sample was converted to the oxalate salt in 2-propanol and was recrystallized twice from 2-propanol. The second time additional oxalic was added to assure the complete conversion to the 1½ oxalate salt, mp 175°–177° C. with effervescence.

Analysis: Calc. for $C_{22}H_{20}ClNO.1.5C_2H_2O_4$: C, 61.92; H, 4.75; N, 2.89. Found: C, 61.88; H, 4.75; N, 2.89.

PREPARATION 4

3-(2-Chlorophenoxy)-1-azetidinecarbonyl chloride

A mixture of 12 g (0.122 mol) of phosgene and 17 g (0.122 mol) of potassium carbonate in 350 ml of methylene chloride was stirred under nitrogen for 30 min then cooled in an ice water bath while 35.6 g (0.102 mol) of 1-(diphenylmethyl)-3-(2-chlorophenoxy)azetidine in 50 ml of methylene chloride was added dropwise. The reaction mixture was removed from the bath and stirred for 3 h; then treated with small pieces of ice to control the decomposition of the excess phosgene. When no further evolution of carbon dioxide was evident, the reaction mixture was treated with 20 ml of water and the methylene chloride solution decanted from the inorganic paste. After concentrating in vacuo, trituration of the residue (51 g) with hexane yielded, upon filtration, 20.7 g (82.5%) of white crystalline product, mp 80°–82° C. A sample was recrystallized from hexane for elemental analysis, mp 80°–82° C.

Analysis: Calculated for $C_{10}H_9Cl_2NO_2$: C, 48.81; H, 3.69; N, 5.69. Found: C, 48.88; H, 3.65; N, 5.67.

PREPARATION 5

3-(4-Chlorophenoxy)-1-(diphenylmethyl)azetidine

A stirred mixture of 119.7 g (0.5 mole) of 1-(diphenylmethyl)azetidin-3-ol and 55.7 g (0.55 mole) of triethylamine in 1.5 L of toluene was cooled in an ice bath under nitrogen while 63 g (0.55 mole) of methanesulfonyl chloride in 50 ml of toluene was added dropwise. After stirring for 18 h the reaction mixture was diluted with 400 ml of 2-propyl ether, and 400 ml of ice water was added to dissolve the triethylamine hydrochloride formed in the reaction. The aqueous portion was separated, the organic phase washed with ice water (6×400 ml), and then returned to the reaction flask. The toluene solution was treated with 70.7 g (0.55 mole) of 4-chlorophenol, 91 g (0.23 mole) of Aliquat 336® (tricaprylylmethylammonium chloride) and 60 g (1.5 mole) of sodium hydroxide dissolved in 300 ml of water. The mixture was stirred vigorously while heating at reflux for 20 h and stirred an additional 72 h at ambient temperature. The basic aqueous portion was separated and the organic phase diluted with an additional 400 ml of 2-propyl ether then washed with warm water (8×400 ml). The organic portion was dried over magnesium sulfate, filtered, and concentrated in vacuo, 173 g. The residual oil was triturated with benzene/ligroin (50/50) yielding 111.8 g (63.9%) of product. The filtrate was treated with oxalic acid dissolved in 2-propanol to yield an additional 17 g (8%) as the oxalate salt. A sample of the free base was recrystallized from 95% ethanol for analysis yielding white crystals, mp 113°–114° C.

Analysis: Calculated for $C_{22}H_{20}ClNO$: C, 75.53; H, 5.76; N, 4.00. Found: C, 75.52; H, 5.63; N, 4.01.

PREPARATION 6

3-(4-Chlorophenoxy)-1-azetidinecarbonyl chloride

A solution of 32.34 g (0.33 mole) of phosgene in 200 ml of methylene chloride cooled with a tap water bath was treated with 45.5 g (0.33 mole) of potassium carbonate and stirred for 30 min. Then 105 g (0.3 mole) of 3-(4-chlorophenoxy)-1-(diphenylmethyl)azetidine in 600 ml of methylene chloride was added dropwise. After stirring for an additional 18 h, the reaction mixture was filtered to remove the inorganic salts then concentrated in vacuo to a oily residue, 127.7 g. A solid formed upon standing which was triturated with boiling petroleum ether 3 times to remove the diphenylmethyl chloride. The residue, 33 g of dark brown crystalline material, was mainly starting material. Upon standing a white crystalline material separated from the petroleum ether triturates (4.4 g, mp 78°–80° C., sent for elemental analysis). The triturates were concentrated in vacuo yielding 31 g of pale yellow tacky crystals. Trituration of these crystals with 2-propyl ether yielded 21.9 g (36%) of pale yellow crystalline product.

Analysis: Calculated for $C_{10}H_9Cl_2NO_2$: C, 48.807; H, 3.687; N, 5.692. Found: C, 49.10; H, 3.61; N, 5.63.

PREPARATION 7

3-(3-Chlorophenoxy)-1-(diphenylmethyl)azetidine ethanedioate (1:1)

A mixture of 48 g (0.2 mole) of 1-(diphenylmethyl)-3-azetidinol and 22 g (0.22 mole) of triethylamine in 800 ml of toluene was stirred in a tap water bath while 27.5 g (0.22 mole) of methanesulfonyl chloride was added dropwise, then stirring was continued for 18 h. The reaction mixture was diluted with 500 ml of ice water to dissolve the triethylamine hydrochloride and destroy any excess methanesulfonyl chloride. The toluene layer was separated and washed with a second 300 ml portion of ice water. The toluene layer was returned to the reaction flask and treated with 25.7 g (0.2 mole) of 3-chlorophenol, 6.5 g (0.02 mole) of tetra-n-butylammonium bromide and 24 g (0.6 mole) of sodium hydroxide in 100 ml of water. This mixture was stirred vigorously at reflux for 38 h and allowed to cool while stirring for an additional 36 h. The basic aqueous portion was separated and the toluene portion washed with water (3×200 ml), dried by filtering through Whatman PS paper and concentrated in vacuo to yield a yellow residue (93 g). The residue was dissolved in 200 ml of 2-propanol, treated with 20 g of oxalic acid, and heated until a clear solution was obtained. After cooling, the precipitated solid was collected by filtration (22.6 g). An additional 15.9 g was obtained from the filtrate on standing. The total yield was 38.5 g of oxalate salt (42%).

Analysis: Calculated for $C_{22}H_{20}ClNO.C_2H_2O_4$: C, 65.53; H, 5.04; N, 3.18. Found: C, 65.53; H, 4.98; N, 3.23.

PREPARATION 8

3-(3-Chlorophenoxy)-1-azetidinecarbonyl chloride

A slurry of 15.9 g (0.036 mole) of 1-(diphenylmethyl)-3-(3-chlorophenoxy)azetidine ethanedioate in 200 ml of water was treated with 10 g of potassium carbonate and 500 ml of toluene. This mixture was heated while stirring until the emulsion which had formed cleared and formed two clear phases. The toluene phase was separated, washed with hot water and concentrated in vacuo. The residue was dissolved in 50 ml of methlene chloride and added dropwise to a stirred mixture of 4 g (0.04 mole) of phosgene and 5.5 g (0.04 mole) of potassium carbonate in 50 ml of methylene chloride under nitrogen. After 2 hr the reaction mixture was treated with ice water to destroy the excess phosgene and dissolve the inorganic salts. The methylene chloride solution was separated, dried over magnesium sulfate and concentrated in vacuo to yield 13 g of residue. A sample was crystallized by cooling to $-78°$ C. and was used to seed the residue which formed a semi-solid paste. Trituration of the paste with petroleum ether yielded 3.5 g (66.5%) of white powder upon filtration. Recrystallization from petroleum ether yielded 0.6 g of white crystalline product, mp 64°-65° C.

Analysis: Calculated for $C_{10}H_9Cl_2NO$: C, 48.81; H, 3.69; N, 5.69. Found: C, 48.83; H, 3.71; N, 5.74.

PREPARATION 9

3-(2-Chloro-6-methylphenoxy)-1-(diphenylmethyl)azetidine

A mixture of 48 g (0.2 mole) of 1-(diphenylmethyl)azetidin-3-ol and 22 g (0.22 mole) of triethylamine in 800 mL of toluene was cooled to 5° C. in an ice bath while stirring under nitrogen. The cooled reaction mixture was treated dropwise with 25.2 g (0.22 mole) of methanesulfonyl chloride in 25 mL of toluene. The reaction mixture was removed from the ice bath. After stirring for 3 hr, the reaction mixture was treated with ice water to dissolve the triethylamine hydrochloride then the aqueous phase was separated and the toluene phase washed with ice water ($2\times 200$ mL). The toluene solution was returned to the reaction flask and treated with 31.4 g (0.22 mole) of 2-chloro-6-methylphenol, 50 mg of tetrabutylammonium bromide and 26.4 g (0.66 mole) of sodium hydroxide in 100 mL of water. The reaction mixture was heated at reflux while stirring vigorously for 24 hr then stirred an additional 72 hr without heat. The mixture was transferred to a separatory funnel and the basic aqueous portion separated. The toluene portion was washed with water ($3\times 100$ mL), dried over magnesium sulfate and concentrated in vacuo to obtain 64.8 g. The crude product was purified by column chromatography using 800 g of Florisil and eluted with benzene to remove trace impurities and then eluted with an acetone gradient from 1-5%. The product came off in 5% acetone/benzene and was collected in 6 fractions which were combined and concentrated in vacuo, 55 g. The oily product which began to crystallize was triturated with ligroin to aid crystallization. Filtration yielded 45.6 g of product (62.7%). A sample recrystallized from ligroin then from 95% ethanol still showed a trace of impurity by t.l.c. (10% methanol/methylene chloride on silica gel). A sample was chromatographed on a 50 g column of Florisil. Elution with 2% acetone/benzene gave the pure product which was recrystallized from 95% ethanol yielding fine white crystals, mp 92°-93° C.

Analysis: Calculated for $C_{23}H_{22}ClNO$: C, 75.92; H, 6.09; N, 3.85. Found: C, 75.96; H, 6.09; N, 3.88.

PREPARATION 10

3-(2-Chloro-6-methylphenoxy)-1-azetidinecarbonyl chloride

A mixture of 13.9 g (0.14 mole) of phosgene and 17.3 g (0.125 mole) of potassium carbonate in 140 mL of methylene chloride was stirred under nitrogen for 30 min then cooled in an ice water bath while 46.5 g (0.125 mole) of 3-(2-chloro-6-methylphenoxy)-1-(diphenylmethyl)azetidine in 140 mL of methylene chloride was added dropwise. After stirring for 16 h the excess phosgene was destroyed by adding small pieces of ice. Water was added to dissolve the inorganic material and the methylene chloride portion was separated, dried (filtered through Whatman PS paper) and concentrated in vacuo, 65.8 g. The oily residue was triturated with 300 mL of 30/60 pet ether and then with 300 mL of hexanes, both at ambient temperature. The remaining yellow residue was triturated with boiling hexanes and the hot solution decanted ($4\times 200$ mL). Upon cooling an orange oil separated which was removed from the hexanes solution by decanting. After decanting again, the hexanes solution was cooled in an ice bath and decanted to remove all traces of the impure orange oil. The volume of hexanes was reduced to 75 mL by heating under a stream of nitrogen. Upon cooling, crystalline product was obtained in 2 fractions (10.8 g and 5.5 g). Rework of the filtrate and the ambient temperature filtrates (300 mL of pet ether and 300 mL of hexanes) yielded an additional 6 g of product for a total yield 22.3 g crude (68.6%), mp 67°-69°. A sample was recrystallized for analysis from hexanes, mp 70°-71.5° C.

Analysis: Calculated for $C_{11}H_{11}Cl_2NO_2$: C, 50.79; H, 4.26; N, 5.39. Found: C, 50.46; H, 4.27; N, 5.37.

PREPARATION 11

3-[2-Chloro-5-(trifluoromethyl)phenoxy]-1-(diphenylmethyl)azetidine monohydrochloride A mixture of 48 g (0.2 mole) of 1-(diphenylmethyl)azetidin-3-ol and 22 g (0.22 mole) of triethylamine in 800 mL of toluene was cooled to 5° C. in an ice bath while stirring under nitrogen. The cooled reaction mixture was treated with 25.2 g (0.22 mole) of methanesulfonyl chloride, added dropwise. The ice bath was removed and after stirring for 3 h, the reaction mixture was diluted with 200 mL of 2-propyl ether and then ice water (500 mL) was added to dissolve the triethylamine hydrochloride which had formed in the reaction. The reaction mixture was transferred to a separatory funnel, the aqueous phase was removed, then the toluene phase was washed with ice water ($2\times 200$ mL). The toluene solution was returned to the reaction flask and treated with 43.2 g (0.22 mole) of 4-chloro-3-hydroxybenzotrifluoride, 28.3 g (0.07 mole) of Aliquat ® 336 (tricaprylylmethylammonium chloride) and 24 g (0.6 mole) of sodium hydroxide in 100 mL of water. The reaction mixture was heated at reflux while stirring vigorously for 16 h. The cooled reaction mixture was transferred to a separatory funnel, the basic aqueous layer was removed, and the organic portion washed with water ($3\times 200$ mL). The toluene solution was stirred while 27 g of oxalic acid in 150 mL of 2-propanol was added. After stirring for 64 hr, the solid precipitate was removed by filtration, yielding 72 g (69.1%) of crude oxalate salt. A sample was recrystallized from 2-propanol; however, even after recrystallization some triethylamine was found to be present as the oxalate salt by proton nmr. The analytical sample was converted to the free base, dissolved in benzene and then washed with water (3×50 mL). The benzene solution was dried (Whatman P. S. paper) and concentrated in vacuo. The pale yellow oil was dissolved in 2 propanol, treated with ethereal hydrogen chloride, warmed to 60° C., then 2-propyl ether was added until just cloudy and warmed just slightly to give a clear solution. Upon cooling fine white crystals of product were collected by filtration, mp 174°–175°.

Analysis: Calculated for $C_{23}H_{19}ClF_3NO \cdot HCl$: C, 60.81; H, 4.44; N, 3.08. Found: C, 60.64; H, 4.36; N, 3.06.

PREPARATION 12

3-[2-Chloro-5-(trifluoromethyl)phenoxy]-1-azetidinecarbonyl chloride

A mixture of 13.5 g (0.14 mol) of phosgene and 19.4 g (0.14 mol) of potassium carbonate in 300 mL of methylene chloride was stirred under nitrogen while cooling in an ice bath. The cold reaction mixture was treated with a solution of 47.6 g (0.114 mol) of 3-[2-chloro-5-(trifluoromethyl)phenoxy]-1-(diphenylmethyl)azetidine in 100 mL of methylene chloride added dropwise. After stirring for 16 hr as the reaction mixture warmed to ambient temperature, it was again cooled in an ice bath while small pieces of ice were added to destroy the excess phosgene. The methylene chloride solution was decanted from the inorganic salt paste, dried by filtering through Whatman PS paper and concentrated in vacuo (58 g). The residue was triturated with 600 mL (3×200 mL) of petroleum ether, decanting the petroleum ether each time. The residue was then triturated with boiling hexanes and allowed to cool. The insoluble oil was separated using a separating funnel yielding 24 g of oily product (67%). A sample was distilled in a Kugelrohr apparatus (136°-150° C. @ 2 mm Hg) yielding a clear oil which slowly solidified on standing, mp 40°–45°.

Analysis: Calculated for $C_{11}H_8Cl_2F_3NO_2$: C, 42.07; H, 2.57; N, 4.46. Found: C, 41.82; H, 2.57; N, 4.46.

PREPARATION 13

1-(Diphenylmethyl)-3-[2-fluoro-5-(trifluoromethyl)-phenoxy]azetidine

A stirred mixture of 48 g (0.2 mole) of 1-(diphenylmethyl)azetidin-3-ol and 22 g (0.22 mole) of triethylamine in 800 mL of toluene was cooled to 5° C. in an ice bath under nitrogen while 28 g (0.22 mole) of methanesulfonyl chloride in 30 mL of toluene was added dropwise. After stirring for 22 h, the reaction mixture was diluted with 200 mL of 2-propyl ether and 300 mL of ice water was added to dissolve the triethylamine hydrochloride formed in the reaction. The aqueous portion was separated and the organic phase washed with ice water (3×200 mL) then returned to the reaction flask. The toluene solution was treated with 39.6 g (0.22 mole) of 2-fluoro-5-(trifluoromethyl)phenol, 28.3 g (0.07 mole) of Aliquat® 336 (tricaprylymethylammonium chloride) and 26.4 g (0.66 mole) of sodium hydroxide dissolved in 50 mL of water. The mixture was stirred vigorously while heating at reflux for 24 h an stirred an additional 48 h at ambient temperature. The basic aqueous layer was then removed. The organic layer was diluted with 200 ml of isopropyl ether, washed with warm water (4×200 mL), dried over magnesium sulfate, and concentrated in vacuo to give 91.7 g of amber oil. The oil was triturated with boiling hexanes and upon cooling, 40.2 g of white crystals were obtained, mp 88°–90° C. A sample was recrystallized for analysis from hexanes yielding fine white crystals, mp 88.5°–90° C. The filtrate was concentrated to an amber oil again and when triturated with ligroin yielded an additional 9.5 g of product. The total yield was 49.7 g (62%).

Analysis: Calculated for $C_{23}H_{19}F_4NO$: C, 68.82; H, 4.77; N, 3.49. Found: C, 68.88; H, 4.64; N, 3.52.

PREPARATION 14

3-[2-Fluoro-5-(trifluoromethyl)phenoxy]-1-azetidinecarbonyl chloride

A mixture of 10.8 g (0.11 mole) of phosgene and 14.2 g (0.11 mole) of potassium carbonate in 200 mL of methylene chloride was cooled to 5° C. in an ice bath while stirring undr nitrogen. After 30 min, the reaction mixture was treated with 40 g (0.1 mole) of 1-(diphenylmethyl)-3-[2-fluoro-5-(trifluoromethyl)phenoxy]azetidine in 100 mL of methylene chloride added dropwise. After stirring for 16 h, the reaction mixture was treated with small pieces of ice to destroy any excess phosgene. Then the reaction mixture was decanted from the inorganic paste and concentrated in vacuo to give 48.6 g of pale yellow oil. The residual oil was distilled at 0.15 mmHg to yield 3 fractions: #1, 12.7 g at 120°–128°; #2, 1.5 g at 128°, and #3 at 128°–132°; with total yield of 19.7 g (66.2%). A sample of fraction #2 was submitted for analysis.

Analysis: Calculated for $C_{11}H_{18}ClF_4NO_2$: C,44.39; H,2.71; N,4.71. Found: C,44.53; H,2.57; N,4.63.

PREPARATION 15

3-(2-Chloro-4-fluorophenoxy)-1-(diphenylmethyl)azetidine ethanedioate (2:3)

A mixture of 48 g (0.2 mole) of 1-(diphenylmethyl)azetidin-3-ol and 22 g (0.22 mole) of triethylamine in 800 mL of toluene was cooled to 5° C. in an ice bath while stirring under nitrogen. The cooled reaction mixture was treated dropwise with 25.2 g (0.22 mole) of methanesulfonyl chloride in 25 mL of toluene. The reaction mixture was removed from the ice bath. After stirring for 3 hr, the reaction mixture was treated with ice water to dissolve the triethylamine hydrochloride which had formed, then the aqueous phase was separated and the toluene phase washed with ice water (2×200 mL). The toluene solution was returned to the reaction flask and treated with 28.9 g (0.22 mole) of 2-chloro-4-fluorophenol, 50 mg of tetrabutylammonium bromide and 26.4 g (0.66 mole) of sodium hydroxide in 100 mL of water. The reaction mixture was heated at reflux while stirring vigorously for 36 hr then stirred an additional 36 hr without heat. The reaction mixture was transferred to a separatory funnel and the basic aqueous portion speared. The toluene portion was washed with water (3×100 mL), dried over magnesium sulfate and concentrated in vacuo, 59.6 g. The crude product was purified by column chromatography using 800 g of Florisil and eluted with benzene and then an acetone/benzene gradient (1 to 10%) with the product appearing in the 5–10% acetone effluents collected in two-500 mL fractions. The combined fractions yielded 30.3 g (41.2%) of oily product. A sample of this product in 2-propanol was treated with 2 equivalents of oxalic acid. The solid which formed was collected by filtration and recrystallized from 2-propanol yielding fine white crystals, mp 176°–177° C. with effervescence.

Analysis: Calculated for $C_{22}H_{19}ClFNO \cdot 1\frac{1}{2}C_2H_2O_4$: C, 59.71; H, 4.41; N, 2.79. Found: C, 59.68; H, 4.38; N, 2.82.

PREPARATION 16

3-(2-Chloro-4-fluorophenoxy)-1-azetidinecarbonyl chloride

A stirred solution of 9.0 g (0.09 mole) of phosgene in 200 mL of methylene chloride under nitrogen was treated with 12.5 g (0.09 mole) of anhydrous potassium carbonate and stirred for 30 min. The reaction mixture was cooled in an ice bath while 28 g (0.08 mole) of 3-(2-chloro-4-fluorophenoxy)-1-(diphenylmethyl)azetidine in 100 mL of methylene chloride was added dropwise. After stirring for 16 hr at ambient temperature the reaction mixture was cooled to 0° C. in an ice water bath and small pieces of ice were added to destroy the excess phosgene, being careful to control the evolution of carbon dioxide gas. When the evolution of gas ceased, the reaction mixture was decanted from the inorganic slurry, dried (filtered through Whatman PS paper) and concentrated in vacuo, 41.9 g. Upon standing, a semisolid residue formed and the solid was collected by filtration after trituration with hexane to obtain 13.2 g (62.5%). A sample was recrystallized from hexane for analysis yielding fine white crystals, mp 93°–94° C.

Analysis: Calculated for $C_{10}H_8Cl_2NO_2$: C, 45.48; H, 3.05; N, 5.30. Found: C, 45.43; H, 3.02; N, 5.30.

PREPARATION 17

3-(3,4-Dichlorophenoxy)-1-(diphenylmethyl)azetidine

A mixture of 48 g (0.2 mole) of 1-(diphenylmethyl)-3-azetidinol and 22 g (0.22 mole) of triethylamine in 800 mL of toluene was stirred in a tap water bath while 27.5 g (0.22 mole) of methanesulfonyl chloride was added dropwise and stirring was continued for 18 h. The reaction mixture was treated with 400 mL of isopropyl ether then filtered. The filter cake was washed with 2×150 mL of 50/50 isopropyl ether and toluene. The combined filtrates were treated with 32.6 g (0.2 mole) of 3,4-dichlorophenol, 100 mg of tetra-n-butylammonium bromide and 24 g (0.6 mole) of sodium hydroxide in 100 mL of water. This mixture was stirred vigorously at reflux for 16 h. The basic aqueous portion was separated and the organic portion washed with water, dried over magnesium sulfate then concentrated to a solid residue, 74.5 g. Several recrystallizations from ethanol-water gave a product which was contaminated with starting azetidinol. Therefore, the material (57.4 g) was dissolved in toluene and treated with silica gel. After stirring for 6 h, the silica gel was removed by filtration and washed with 50/50 ethyl acetate and toluene. The filtrates were concentrated to yield 45.9 g (59.7%) of pure product. A sample for elemental analysis was recrystallized from 190 ethanol, mp. 114°–115° C.

Analysis: Calculated for $C_{22}H_{19}Cl_2NO$: C, 68.759; H, 4.983; N, 3.645. Found: C, 68.73; H, 5.00; N, 3.65.

PREPARATION 18

3-(3,4-Dichlorophenoxy)-1-azetidinecarbonyl chloride

A solution of 14 g (0.144 mole) of phosgene weighed into 200 mL of methylene chloride was treated with 19.9 g (0.144 mole) of anhydrous potassium carbonate and stirred for 1 h then 45.9 g (0.12 mole) of 1-(diphenylmethyl)-3-(3,4-dichlorophenoxy)azetidine in 100 mL of methylene chloride was added dropwise and stirring was continued for 72 h. The reaction mixture was filtered to remove the inorganic salts and then concentrated in vacuo to a pale yellow oil (67 g). Trituration of the residue with cyclohexane yielded a crude pale yellow solid (23.6 g). The filtrate was treated with ligroin and upon standing an additional 13.3 g of tacky material was obtained (contaminated with diphenylmethyl chloride). After several recrystallizations from cyclohexane to remove traces of diphenylmethyl chloride a portion was obtained as fine white crystals, mp 96°–99° C.

Analysis: Calculated for $C_{10}H_{18}Cl_3NO_2$: C, 42.81; H, 2.87; N, 4.99. Found: C, 43.32; H, 2.89; N, 4.99.

EXAMPLE 1

3-[2-Chloro-4-(trifluoromethyl)phenoxy]-1-azetidinecarboxamide

A solution of 2 g (0.0065 mole) of 3-[2-chloro-4-(trifluoromethyl)phenoxy]-1-azetidinecarbonyl chloride in 15 ml of tetrahydrofuran was treated while stirring with 1 ml (0.013 mole) of 57% ammonium hydroxide. After stirring for 16 h the reaction mixture was diluted with 100 ml of water and the solid which precipitated was collected by filtration (2.4 g). Recrystallization from benzene/ligroin yielded 1.6 g (83.5%) of white crystals, mp. 156°–159° C.

Analysis: Calculated for $C_{11}H_{10}ClF_3N_2O_2$: C, 44.84; H, 3.42; N, 9.51. Found: C, 44.78; H, 3.38; N, 9.52.

EXAMPLE 2

3-[2-Chloro-4-(trifluoromethyl)phenoxy]-N-methyl-1-azetidinecarboxamide

A solution of 2 g (0.0065 mole) of 3-[2-chloro-4-(trifluoromethyl)phenoxy]-1-azetidinecarbonyl chloride in 15 ml of tetrahydrofuran was treated while stirring with 1 ml (0.013 mole) of 40% aqueous monomethylamine. After stirring for 16 h the reaction mixture was diluted with 100 ml of water and the solid which precipitated was collected by filtration (2.4 g). Recrystallization from benzene/ligroin yielded 2.2 g of white crystals, mp 160°–161°.

Analysis: Calculated for $C_{12}H_{12}ClF_3N_2O_2$: C, 46.69; H, 3.92; N, 9.08. Found: C, 46.69; H, 3.90; N, 9.03.

EXAMPLE 3

3-[2-Chloro-4-(trifluoromethyl)phenoxy]-N-(2-propenyl)-1-azetidinecarboxamide

A mixture of 2 g (0.0065 mole) of 3-[2-chloro-4-(trifluoromethyl)phenoxy]-1-azetidinecarbonyl chloride and 0.9 g (0.0065 mole) of potassium carbonate in 20 ml of tetrahydrofuran was treated while stirring with 0.35 g (0.0065 mole) of 2-propenylamine. After stirring for 16 h, the reaction mixture was diluted with 100 ml of water whereupon an oil separated. The oil slowly solidified and was collected by filtration (2.3 g wet). The rose colored solid was recrystallized from benzene/ligroin yielding 1.7 g (78.1%) of beige crystals, mp 102°–104°.

Analysis: Calculated for $C_{14}H_{14}ClF_3N_2O_2$: C, 50.24; H, 4.22; N, 8.34. Found: C, 50.23; H, 4.20; N, 8.33.

EXAMPLE 4

3-[2-Chloro-4-(trifluoromethyl)phenoxy]-N,N-dimethyl-1-azetidinecarboxamide

A stirred solution of 5 g (0.016 mol) of 3-[2-chloro-4-(trifluoromethyl)phenoxy]-1-azetidinecarbonyl chloride in 20 ml of tetrahydrofuran was treated with 5.5 ml (0.048 mol) of 40% aqueous dimethylamine. After stirring for 16 h, the reaction mixture was diluted with 200 ml of water and the solid which precipitated was collected by filtration (4.8 g). The crude product was crystallized from benzene/ligroin to yield 4.3 g (83.3%) of fine white crystals, mp 106°–108° C.

Analysis: Calculated for $C_{13}H_{14}ClF_3N_2O_2$: C, 48.39; H, 4.37; N, 8.68. Found: C, 48.39; H, 4.32; N, 8.47.

EXAMPLE 5

3-[2-(Trifluoromethyl)phenoxy]-N-methyl-1-azetidinecarboxamide

To 4.5 g (0.02 mole) of 3-[2-(trifluoromethyl)phenoxy]azetidine stirring in 50 ml of dry benzene, was added slowly 1.2 g (0.02 mole) of methyl isocyanate at room temperature. Stirring was continued for 30 minutes. A solid formed, and after filtration was recrystallized from benzene to yield 3.5 g (68%), mp 134°–136°.

Analysis: Calculated for $C_{12}H_{13}F_3N_2O_2$: C, 52.56; H, 4.78; N, 10.22. Found: C, 52.28; H, 4.78; N, 10.07.

EXAMPLE 6

N-Methyl-3-[3-(trifluoromethyl)phenoxy]-1-azetidinecarboxamide

To 6.0 g (0.024 mole) of 3-[3-(trifluoromethyl)phenoxy]azetidine in 50 ml of dry benzene was added dropwise 1.37 g (0.024 mole) of methylisocyanate, and stirring was continued for 30 minutes. The solid which crystallized in the flask was recrystallized from 95% ethanol to obtain 5.0 g (76%), mp 145°–147°.

Analysis: Calculated for $C_{12}H_{13}F_3N_2O_2$: C, 52.56; H, 4.78; N, 10.22. Found: C, 52.67; H, 4.78; N, 10.16.

EXAMPLE 7

3-(4-Trifluoromethylphenoxy)-N-methyl-1-azetidinecarboxamide

The oxalic acid salt of 3-[4-(trifluoromethyl)phenoxy]azetidine, weighing 13.0 g (0.042 mole), was partitioned between 50 ml of benzene and 50 ml of potassium hydroxide solution. The benzene layer was dried with Drierite and filtered, and to this stirring filtrate was added 2.6 g (0.046 mole) of methyl isocyanate. Stirring was continued overnight. The mixture was concentrated in vacuo, and the solid residue was recrystallized from a mixture of isopropyl ether-ethyl acetate to give 7.5 g (65%), mp 154°–157°.

Analysis: Calculated for $C_{12}H_{13}F_3N_2O_2$: C, 52.56; H, 4.78; N, 10.21. Found: C, 52.62; H, 4.75; N, 10.17.

EXAMPLE 8

3-(2-Chlorophenoxy)-N-methyl-1-azetidinecarboxamide

A stirred solution of 4.5 g (0.018 mol) of 3-(2-chlorophenoxy)-1-azetidinecarbonyl chloride in 20 ml of tetrahydrofuran was treated with 4 ml (0.05 mol) of 40% aqueous monomethylamine and stirred for 16 h. The reaction mixture was diluted with 200 ml of water and the precipitated product collected by filtration (4.3 g). The crude product was recrystallized from benzene/ligroin yielding 3.9 g (90.0%) of fine white crystals, mp 129.5°–131.5° C.

Analysis: Calculated for $C_{11}H_{13}ClN_2O_2$: C, 54.89; H, 5.44; N, 11.64. Found: C, 55.00; H, 5.48; N, 11.60.

EXAMPLE 9

3-(3-Chlorophenoxy)-N-methyl-1-azetidinecarboxamide

A solution of 3-(3-chlorophenoxy)-1-azetidinecarbonyl chloride (0.01275 mole) in 20 ml of THF was treated with 4 ml (0.05 mole) of 40% aqueous methylamine and stirred for 16 h. The reaction was diluted with $H_2O$ until an oil began to separate then extracted with 3×50 ml of benzene. The combined extracts were dried over $MgSO_4$ and concentrated to a solid which was recrystallized from benzene/ligroin to yield 1.2 g (40%) of fine white crystals, mp 140°–141° C.

Analysis: Calculated for $C_{11}H_{13}ClN_2O_2$: C, 54.89; H, 5.44; N, 11.64. Found: C, 55.05; H, 5.58; N, 11.52.

EXAMPLE 10

3-(4-Chlorophenoxy)-N-methyl-1-azetidinecarboxamide

A stirred solution of 5 g (0.02 mole) of 3-(4-chlorophenoxy)-1-azetidinecarbonyl chloride in 20 ml of tetrahydrofuran was treated with 4.7 g (0.06 mole) of 40% aqueous monomethylamine. After stirring for 18 h, the reaction mixture was diluted with 200 ml of water and the solid which separated was collected by filtration, 5.7 g. Recrystallization from benzeneligroin was accomplished by adding magnesium sulfate to absorb the water which separated from the wet product. After filtering and cooling the hot filtrate, the precipitated solid was collected by filtration to yield 4.1 g (85%) of white crystals, mp 144°–145° C.

Analysis: Calculated for $C_{11}H_{13}ClN_2O_2$: C, 54.89; H, 5.44; N, 11.64. Found: C, 54.89; H, 5.43; N, 11.65.

EXAMPLE 11

3-(2,4-Dichlorophenoxy)-1-azetidinecarboxamide

A stirred solution of 4.8 g (0.017 mole) of 3-(2,4-dichlorophenoxy)-1-azetidinecarbonyl chloride in 20 mL of tetrahydrofuran was treated with 3.0 mL (0.05 mole) of 57% ammonium hydroxide. After stirring for 5 h, the reaction mixture was diluted with 200 mL of water and the precipitated solid collected by filtration (4.1 g). The crude product was recrystallized from acetonitrile/water to yield 3.9 g (87.9%) of white crystals, mp 169°–170° C.

Analysis: Calculated for $C_{10}H_{10}Cl_2N_2O_2$: C, 46.00; H, 3.86; N, 10.73. Found: C, 45.93; H, 3.83; N, 10.69.

EXAMPLE 12

3-(2,4-Dichlorophenoxy)-N,N,-dimethyl-1-azetidinecarboxamide

A stirred solution of 4.8 g (0.017 mole) of 3-(2,4-dichlorophenoxy)-1-azetidinecarbonyl chloride in 20 mL of tetrahydrofuran was treated with 5.8 mL (0.05 mole) of 40% aqueous dimethylamine. After stirring for 5 h, the reaction mixture was diluted with 200 mL of water and the oil which separated was extracted into methylene chloride (3×30 mL). The combined extracts were dried (Whatman PS paper) and concentrated in vacuo, (5 g). The crude oil solidified on standing and was recrystallized from ligroin yielding 3.4 g (69.2%) of silver plate-like crystals, mp 62°–63° C.

Analysis: Calculated for $C_{12}H_{14}Cl_2N_2O_2$: C, 49.85; H, 4.88; N, 9.69. Found: C, 49.80; H, 4.89; N, 9.65.

EXAMPLE 13

3-(2,4-Dichlorophenoxy)-N-methyl-1-azetidinecarboxamide

A stirred solution of 4.8 g (0.017 mole) of 3-(2,4-dichlorophenoxy)-1-azetidinecarbonyl chloride in 20 mL of tetrahydrofuran was treated with 4 mL (0.05 mole) of 40% aqueous monomethylamine. After stirring for 5 h, the reaction mixture was diluted with 200 mL of water and the precipitated solid collected by filtration (4.6 g). The crude product was recrystallized from acetonitrile yielding 3.4 g (72.7%) of coarse white powder, mp 140°–141° C.

Analysis: Calculated for $C_{11}H_{12}Cl_2N_2O_2$: C, 48.02; H, 4.40; N, 10.18. Found: C, 47.94; H, 4.38; N, 10.15.

EXAMPLE 14

3-(2-Chloro-6-methylphenoxy)-1-azetidinecarboxamide

A stirred solution of 3.9 g (0.015 mole) of 3-(2-chloro-6-methylphenoxy)-1-azetidinecarbonyl chloride in 20 mL of tetrahydrofuran was treated all at once with 2.8 mL (0.045 mole) of 57% ammonium hydroxide. After stirring for 72 h the reaction mixture was diluted with 200 mL of water and the precipitated product collected by filtration (3.6 g of pale yellow product). Recrystallization from benzene yielded 2.8 g (69.2%) of fine white crystals, mp 256°–157° C.

Analysis: Calculated for $C_{11}H_{13}ClN_2O_2$: C, 54.89; H, 5.44; N, 11.64. Found: C, 54.85; H, 5.49; N, 11.50.

EXAMPLE 15

3-(2-Chloro-6-methylphenoxy)-N,N-dimethyl-1-azetidinecarboxamide

A stirred solution of 3.9 g (0.015 mole) of 3-(2-chloro-6-methylphenoxy)-1-azetidinecarbonyl chloride in 20 mL of tetrahydrofuran was treated all at once with 5.1 mL (0.045 mole) of 40% aqueous dimethylamine. After stirring for 72 h the raction mixture was diluted with 200 mL of water and the oil which separated was extracted into methylene chloride (3×30 mL). The combined extracts were dried by filtering through Whatman PS paper and concentrated in vacuo (3.6 g). The crude oil solidified when cooled in a dry ice/acetone bath and was recrystallized from ethyl ether in a dry ice-acetone bath yielding, after filtering cold, 2.6 g (64.5%) of coarse white crystals, mp 46°–47° C.

Analysis: Calculated for $C_{13}H_{17}ClN_2O_2$: C, 58.10; H, 6.38; N, 10.42. Found: C, 58.05; H, 6.52; N, 10.25.

EXAMPLE 16

3-(2-Chloro-6-methyphenoxy)-N-methyl-1-azetidinecarboxamide

A stirred solution of 3.9 g (0.015 mole) of 3-(2-chloro-6-methylphenoxy)-1-azetidinecarbonyl chloride in 20 mL of tetrahydrofuran was treated all at once with 3.5 mL (0.045 mole) of 40% aqueous monomethylamine. After stirring for 72 h the reaction mixture was diluted with 200 mL of water and the precipitated solid collected by filtration to give 5.6 g of wet white product. The crude product was recrystallized (after drying) from benzene/ligroin, yielding 2.9 g (75.9%) of white crystalline product, mp 119°–121° C.

Analysis: Calculated for $C_{12}H_{15}ClN_2O_2$: C, 56.59; H, 5.94; N, 11.00. Found: C, 56.62; H, 6.00; N, 11.02.

EXAMPLE 17

3-(2-Chloro-4-fluorophenoxy)-N-methyl-1-azetidinecarboxamide

A stirred solution of 2.9 g (0.011 mole) of 3-(2-chloro-4-fluorophenoxy)-1-azetidinecarbonyl chloride in 20 mL of tetrahydrofuran was treated with 4 mL (0.05 mole) of 40% aqueous monomethylamine and stirred for 16 hr. The reaction mixture was diluted with 200 mL of water. The solid which precipitated was collected by filtration (2.7 g). The crude product was recrystallized from benzene/ligroin yielding 2.4 g (84.3%) of fine white crystals, mp 139°–141° C.

Analysis: Calculated for $C_{11}H_{12}ClFN_2O_2$: C, 51.08; H, 4.68; N, 10.83. Found: C, 51.13; H, 4.70; N, 10.78.

EXAMPLE 18

3-[2-Chloro-5-(trifluoromethyl)phenoxy]-N-methyl-1-azetidinecarboxamide

A stirred solution of 5.2 g (0.017 mol) of 3-(2-chloro-5-trifluoromethylphenoxy)-1-azetidinecarbonyl chloride in 20 mL of tetrahydrofuran was treated all at once with 4 g (0.05 mol) of 40% aqueous monomethylamine and stirred for 16 hr. The reaction mixture was diluted with 200 mL of water and the oil globules which separated slowly solidified on standing. Filtration yielded 4 g of crude product which was recrystallized from benzene/ligroin yielding 3.3 g (62.9%) of fine white crystalline product, mp 132°–133° C.

Analysis: Calculated for $C_{12}H_{12}ClF_3N_2O_2$: C, 46.69; H, 3.92; N, 9.08. Found: C, 46.32; H, 3.87; N, 8.96.

EXAMPLE 19

3-[2-Fluoro-5-(trifluoromethyl)phenoxy]-N-methyl-1-azetidine-carboxamide

A stirred solution of 4.5 g (0.015 mol) of 3-[2-fluoro-5-(trifluoromethyl)phenoxyl]-1-azetidinecarbonyl chloride in 20 mL of tetrahydrofuran was treated with 4.0 g (0.05 mol) of 40% aqueous monomethylamine. After stirring for 16 h the reaction mixture was diluted with 200 mL of water and the oil which separated slowly solidified. The solids were collected by filtration (3.9 g) and recrystallized from benzene/ligroin, yielding 3.5 g (79.8%) of white crystals, mp 93.5°–95° C.

Analysis: Calculated for $C_{12}H_{12}F_4N_2O_2$: C, 49.32; H, 4.14; N, 9.59. Found: C, 49.50; H, 4.09; N, 9.61.

EXAMPLE 20

3-(3,4-Dichlorophenoxy)-N-methyl-1-azetidinecarboxamide

A solution of 5.6 g (0.02 mole) of 3-(3,4-dichlorophenoxy)-1-azetidinecarbonyl chloride in 20 mL of tetrahydrofuran was stirred while 5 mL (0.06 mole) of 40% aqueous methylamine was added slowly and stirring was continued for 18 h. The reaction mixture was diluted with 200 mL of ice water, and the solid which formed was collected by filtration (6.9 g). The crude wet solid was recrystallized from ethanol/water to yield 3.65 g (66.3%) of greenish-gray plate-like crystals, mp 158°–159° C.

Analysis: Calculated for $C_{11}H_{12}Cl_2N_2O_2$: C, 48.021; H, 4.396; N, 10.182. Found: C, 48.18; H, 4.39; N, 10.00.

PHARMACOLOGY

Pharmacological test data for 3-(monosubstituted-phenoxy)-1-azetidine carboxamides are shown in Table 1. The pharmacological test data are expressed either as an $ED_{50}$ (mg/kg) or percent protection/dose (mg/kg) for test compounds administered intraperitoneally (IP) in mice. The data show that 3-(2-substitutedphenoxy)-1-azetidinecarboxamides are less potent than the 3-(3-substituted phenoxy- or 3-(4-substitutedphenoxy)-1-azetidinecarboxamide analogs in the electroshock test.

The noticeably lower potency of the compounds having the substituent in the 2-position on the phenoxy group did not suggest that introduction of a chlorine atom at the 2-position would augment the potency of the 3-[4-(trifluoromethyl)phenoxyl]-1-azetidinecarboxamides. When prepared and tested however, it was found that the 3-(2-chloro-4-(trifluoromethyl)phenoxyl]-1-azetidinecarboxamides were several times as potent in the electroshock test as the 3-[4-(trifluoromethyl)-phenoxyl]-1-azetidinecarboxamides. The pharmacological data are shown in Table 2.

The 3-[2-chloro-4-(trifluoromethyl)phenoxyl]-1-azetidinecarboxamides are more potent in the electroshock test than other 3-(disubstitutedphenoxy)1-azetidinecarboxamides as shown in Table 3.

Specificity in one test over the other given an indication of the type of epilepsy the Formula I compounds will be more useful in treating.

Anticonvulsant drugs which protect against pentylenetetrazol-induced convulsions are generally considered to be useful in treating absence type epileptic seizures and those that protect against electrical-stimulation induced convulsions are useful in treating the partial seizures of epilepsy. Thus, the compounds of Examples 3 and 4 would not be expected to be effective in treating absence seizures whereas the compounds of Examples 1 and 2 might be effective against these seizures as well as the partial type of seizure.

TABLE 1

Pharmacological Data for 3-(Monosubstitutedphenoxy)-1-azetidinecarboxamides

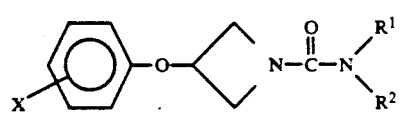

| Ex | X | R² | Electroshock[1] | Metrazole[1] |
|---|---|---|---|---|
| 5 | 2-CF₃ | NHCH₃ | 125 | 0/120 |
| 6 | 3-CF₃ | NHCH₃ | 29 | 90.9 |
| 7 | 4-CF₃ | NHCH₃ | 25.7 | 33 |
| 8 | 2-Cl | NHCH₃ | 0/56.2 | 0/100 |
| 9 | 3-Cl | NHCH₃ | 45.5 | 37.5/100 |
| 10 | 4-Cl | NHCH₃ | 23.8 | 50 |

[1]$ED_{50}$ (mg/kg IP) or % protected/dose (mg/kg IP)

TABLE 2

Pharmacological Data for 3-[2-Chloro-4-(trifluoromethyl)phenoxy]-1-azetidinecarboxamides

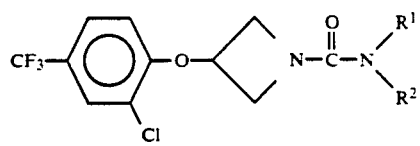

| Ex | R² | Electroshock[1] | Metrazole[1] |
|---|---|---|---|
| 1 | NH₂ | 8.5 | 11.5 |
| 2 | NHCH₃ | 6.4 | 11.3 |
| 3 | NH(CH₂CH=CH₂) | 9.5 | 12.5/10 0/36 |
| 4 | N(CH₃)₂ | 8.2 | 37.5/31.6 0/52 0/100 |

[1]$ED_{50}$ (mg/kg IP) or % protected/dose (mg/kg IP)

TABLE 3

Pharmacological Data for 3-(disubstitutedphenoxy)-1-azetidinecarboxamides

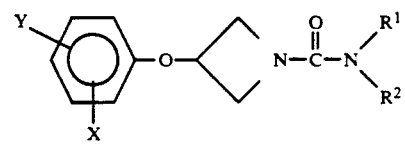

| Ex | X | Y | R² | Electroshock[1] | Metrazole[1] |
|---|---|---|---|---|---|
| 1 | 2-Cl | 4-CF₃ | NH₂ | 8.5 | 11.5 |
| 2 | 2-Cl | 4-CF₃ | NHCH₃ | 6.4 | 11.3 |
| 3 | 2-Cl | 4-CF₃ | NH(CH₂CH=CH₂) | 9.5 | 12.5/10 0/36 |
| 4 | 2-Cl | 4-CF₃ | N(CH₃)₂ | 8.2 | 0/52 0/100 |
| 11 | 2-Cl | 4-Cl | NH2 | 0/17.8 100/31.6 | 31.6 |
| 12 | 2-Cl | 4-Cl | N(CH₃)₂ | 0/17.8 100/31.6 | — |
| 13 | 2-Cl | 4-Cl | NHCH₃ | 18.5 | 40.9 |
| 14 | 2-Cl | 6-CH₃ | NH₂ | 81.5 | — |
| 15 | 2-Cl | 6-CH₃ | N(CH₃)₂ | 37.5-62.5/31.6 | — |
| 16 | 2-Cl | 6-CH₃ | NHCH₃ | 53 | — |
| 17 | 2-Cl | 4-F | NHCH₃ | 44.5 | 32.8 |
| 18 | 2-Cl | 5-CF₃ | NHCH₃ | 37.5/56.2 50/100 | — |
| 19 | 2-F | 5-CF₃ | NHCH₃ | 50/31.6 50/56.2 | — |
| 20 | 3-Cl | 4-Cl | NHCH₃ | 39.5 | 49.5 |

[1]$ED_{50}$ (mg/kg IP) or % protected/dose (mg/kg IP)

PHARMACOLOGY METHODS

Maximal Electroshock

Adult female mice in groups of eight were administered the test drug intraperitoneally (usually 100 mg/kg initially for screening) in liquid carrier (10 mg/ml), usually physiological saline or water, 30 minutes prior to electrical challenge. Animals were challenged electrically by placing brass electrodes on the corneas and applying an electrical stimulus (60 Hz, 5 m sec. pulse width, 34 mA intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The $ED_{50}$, 95% confidence limits and potency ratio may be ascertained by the method of J. T. Litchfield and F. Wilcoxon (1949) J. PHARMACOL. EXP. THER. 96, 99-113.

Metrazole Chemical Challenge (Swinyard Method)

Groups of 8 adult female mice were randomly assigned to dosage groups according to the method of Steel, R. G. D., and Torrie, J. H. (1960) in "Principles and Procedures of Statistics", McGraw-Hill Book Company, Inc., pp 99-100, pp 428-31. Each mouse was identified with a color code on its tail. The test compounds were administered as solutions or suspensions in 10 ml/kg mouse body weight of 0.5% aqueous methyl cellulose within 15 minutes of preparation of the suspension. Metrazole ® (pentylenetetrazol) was prepared as a solution in physiological saline. The mice were not fasted prior to the test. Eight mice were tested at each dosage level.

Each mouse received one dose of the test drug (usually 100 mg/kg for screening) in the 0.5% aqueous methylcellulose or the control article (0.5% aqueous methylcellulose alone) intraperitoneally. Metrazole (80 mg/kg S.C.) was then given in a loose fold of skin on the back of the neck, ½ hour after the test compound or control article was given. All injections were given in a volume of 10 ml/kg mouse body weight. Each mouse was observed for 30 minutes following Metrazol injection. Failure of the animals to exhibit a threshold seizure (a single episode of clonic spasms at least 5 seconds in duration) was defined as protection. Anticonvulsant data were tabulated as the percent protection, i.e., $$\frac{\text{No. Mice Protected} \times 100}{\text{No. Mice Tested}}.$$

The $ED_{50}$, 95% confidence limits and potency ratio may be ascertained by the computer-based probit analysis ascribed to Finney, D. J. (1964) *Statistical Method in Biological Assay*, 2nd Ed., New York. Hefner Publishing Co.

Pharmaceutical Composition

The pharmacologically active 3-[2-chloro-4-(trifluoromethyl)phenoxy]1-azetidinecarboxamides of this invention are effective in the treatment of absence-type and partial-type epileptic seizures. Effective quantities of these compounds may be administered to a living animal body orally as in capsules, tablets or elixirs, parenterally in the form of sterile solutions or suspensions, intravenously in the form of sterile solutions, suppositories, and the like. It is only necessary that the active ingredient constitute an effective amount, i.e., such that a suitable effective dosage will be obtained consistent with the dosage form employed. The exact individual dosage as well as daily dosages will, of course, be determined according to standard medical principles under the direction of a physician or veterinarian.

Based upon a comparison with known anticonvulsant compounds, daily dosages appear to preferably range from about 0.5 to 1.5 milligrams per kilogram of body weight in the treatment of absence (petit mal) epilepsy and about 25 to 35 milligrams per kilogram of body weight in the treatment of partial (grand mal) epilepsy. Very small quantities of the active materials of the present invention, even as low as 0.1 milligram, are effective when minor therapy is involved. Unit dosages are usually 5 milligrams or above and preferably 25, 50 or 100 milligrams per unit dose. The active ingredients of the invention may be combined with other pharmacologically active agents as previously indicated, or with buffers, antacids or the like, for administration and the proportion of the active agent in the composition may be varied widely.

Capsules

Capsules of 5 mg, 25 mg, and 50 mg of active ingredient per capsule are prepared; with higher amounts of ingredient reduction may be made in the amount of lactose.

| Typical blend for encapsulation | Per Capsule, mg. |
|---|---|
| Active ingredient | 5.0 |
| Lactose | 296.7 |
| Starch | 129.0 |
| Magnesium stearate | 4.3 |
| Total | 435.0 mg |

Uniformly blend the selected active ingredient with lactose, starch and magnesium stearate and encapsulate the blend.

Additional capsule formulations preferably contain a higher dose of active ingredient and are as follows:

| Ingredients | 100 mg per Capsule | 250 mg per Capsule | 500 mg per Capsule |
|---|---|---|---|
| Active ingredient | 100.0 | 250.0 | 500.0 |
| Lactose | 231.5 | 126.5 | 31.1 |
| Starch | 99.2 | 54.2 | 13.4 |
| Magnesium stearate | 4.3 | 4.3 | 5.5 |
| Total mg | 435.0 | 435.0 | 550.0 |

Tablets

A typical formulation for a tablet containing 5.0 mg of active ingredient per tablet follows. The formulation may be used for other strengths of active ingredient by adjustment of weight of dicalcium phosphate.

| Ingredients | Per Tablet, mg. |
|---|---|
| (1) Active ingredient | 5.0 |
| (2) Corn Starch | 13.6 |
| (3) Corn Starch (paste) | 3.4 |
| (4) Lactose | 79.2 |
| (5) Dicalcium phosphate | 68.0 |
| (6) Calcium Stearate | 0.9 |
| Total | 170.1 mg |

Uniformly blend 1, 2, 4 and 5. Prepare 3 as a 10 percent paste in water. Granulate the blend with the starch paste and pass the wet mass through a number eight mesh screen. The wet granulation is dried and passed through a number twelve mesh screen. The dried granules are blended with calcium stearate and compressed.

Additional tablet formulations preferably contain a higher dosage of the active ingredient and are as follows:

| 50 mg Tablet | |
| --- | --- |
| Ingredients | Per Tablet, mg |
| Active ingredient | 50.0 |
| Lactose | 90.0 |
| Corn starch | 58.0 |
| Calcium stearate | 2.0 |
| Total | 200.0 |

Uniformly blend the active ingredient, lactose, and corn starch. The blend is granulated, using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

Intravenous Injection

| Ingredients | Per ml |
| --- | --- |
| 1. Active ingredient | 10.0 mg |
| 2. Isotonic pH 4.0 buffer solution | q.s. to 1.0 ml |

Procedure
Step 1. Dissolve the active ingredient in the buffer solution.
Step 2. Aseptically filter the solution from Step 1.
Step 3. The sterile solution is now aseptically filled into sterile ampuls.
Step 4. The ampuls are sealed under aseptic conditions.

Intramuscular Injection

| Ingredients | Per ml |
| --- | --- |
| 1. Active ingredient | 50.0 mg |
| 2. Isotonic pH 4.0 buffer solution | q.s. to 5.0 ml |

Procedure
Step 1. Dissolve the active ingredient in the buffer solution.
Step 2. Aseptically filter the solution from Step 1.
Step 3. The sterile solution is now aseptically filled into sterile ampuls.
Step 4. The ampuls are sealed under aseptic conditions.

Suppositories

| Ingredients | Per Supp. |
| --- | --- |
| 1. Active ingredient | 500.0 mg |
| 2. Polyethylene Glycol 1000 | 1350.0 mg |
| 3. Polyethylene Glycol 4000 | 450.0 mg |
| | 2300.0 mg |

Procedure
Step 1. Melt ingredients 2 and 3 together and stil until uniform.
Step 2. Dissolve 1 in the molten mass from Step 1 and stir until uniform.
Step 3. Pour the molten mass from Step 2 into suppository molds and allow to cool.
Step 4. Remove the suppositories from molds and wrap.

Various modifications and equivalents will be apparent to one skilled in the art and may be made in the compounds, method, and compositions of the present invention without departing from the spirit or scope thereof, and it is therefore to be understood that the invention is to be limited only the scope of the appended claims.

What is claimed is:

1. A compound having the formula:

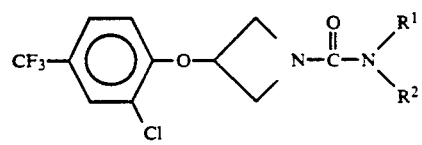

where $R^1$ and $R^2$, same or different, are selected from hydrogen, $C_1$–$C_4$ alkyl, or allyl.

2. A compound according to claim 1 which is 3-[2-chloro-4-(trifluoromethyl)phenoxy]-1-azetidinecarboxamide.

3. A compound according to claim 1 which is 3-[2-chloro-4-(trifluoromethyl)phenoxy]-N-methyl-1-azetidinecarboxamide.

4. A compound according to claim 1 which is 3-[2-chloro-4-(trifluoromethyl)phenoxy]-N-(2-propenyl)-1-azetidinecarboxamide.

5. A compound according to claim 1 which is 3-[2-chloro-4-(trifluoromethyl)phenoxy]-N,N-dimethyl-1-acetidinecarboxamide.

6. A pharmaceutical composition for the treatment of convulsions in warm blood animals comprising:
a. a therapeutically effective amount of a compound of the formula:

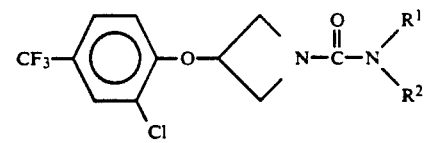

where $R^1$ and $R^2$, same or different, are selected from hydrogen, $C_1$–$C_4$ alkyl, or allyl; and
b. a pharmaceutically acceptable carrier.

* * * * *